(12) United States Patent
Villers et al.

(10) Patent No.: US 8,528,305 B2
(45) Date of Patent: Sep. 10, 2013

(54) FLEXIBLE ULTRA-LOW PERMEABILITY TRANSPORT SYSTEM AND METHOD

(75) Inventors: Philippe Villers, Concord, MA (US); Tom De Bruin, Kibbutz HaOgen (IL); Shlomo Navarro, Holon (IL)

(73) Assignee: GrainPro, Inc., Concord, MA (US)

( * ) Notice: Subject to any disclaimer, the term of this patent is extended or adjusted under 35 U.S.C. 154(b) by 0 days.

(21) Appl. No.: 13/107,379

(22) Filed: May 13, 2011

(65) Prior Publication Data
US 2011/0209445 A1    Sep. 1, 2011

Related U.S. Application Data

(62) Division of application No. 11/368,803, filed on Mar. 6, 2006, now abandoned.

(60) Provisional application No. 60/658,586, filed on Mar. 7, 2005.

(51) Int. Cl.
*B65B 11/58* (2006.01)

(52) U.S. Cl.
USPC .............................. 53/449; 53/469; 53/284.7

(58) Field of Classification Search
USPC .................. 53/449, 442, 459, 469, 399, 557, 53/173, 570, 284.7
See application file for complete search history.

(56) References Cited

U.S. PATENT DOCUMENTS

| | | |
|---|---|---|
| 234,185 A | 11/1880 | Hendrick |
| 1,287,254 A | 12/1918 | Davis |
| 1,340,718 A | 5/1920 | Johnson |
| 2,624,886 A | 1/1953 | Herman |
| 2,730,150 A | 1/1956 | Wunderwald et al. |
| 2,914,776 A | 12/1959 | Hotz |
| 3,485,635 A | 12/1969 | Fassauer |
| 3,490,632 A | 1/1970 | McKinney |
| 3,717,296 A | 2/1973 | Fellbrink |
| 3,727,656 A * | 4/1973 | Luders .......................... 383/105 |
| 3,949,527 A | 4/1976 | Double et al. |
| 4,084,358 A | 4/1978 | Winters |
| 4,208,443 A | 6/1980 | Kanuch et al. |

(Continued)

FOREIGN PATENT DOCUMENTS

| | | |
|---|---|---|
| IL | 87301 | 3/1996 |
| IL | 122456 | 1/2001 |

(Continued)

OTHER PUBLICATIONS

In the U.S. Patent and Trademark Office, Office Action in re: U.S. Appl. No. 11/368,803, dated Mar. 30, 2011, 18 pages.

(Continued)

*Primary Examiner* — Sameh H. Tawfik
(74) *Attorney, Agent, or Firm* — Venable LLP; Michele V. Frank, Esq.

(57) ABSTRACT

A method for storage and transport of a commodity is described. The method may include the steps of placing the commodity in a long-term storage container, hermetically sealing said long-term storage container, and placing the long-term storage container in an outer container. The long-term storage container may include an outer layer, an inner layer, and a middle layer. The middle layer may be made of an ultra-low permeability material. The placing may include providing a capability of storing for at least four months.

9 Claims, 3 Drawing Sheets

(56) References Cited

U.S. PATENT DOCUMENTS

| | | | |
|---|---|---|---|
| 4,224,770 A | 9/1980 | Petty | |
| 4,413,029 A | 11/1983 | Handwerker | |
| 4,508,737 A | 4/1985 | Forest et al. | |
| 4,521,372 A | 6/1985 | Price et al. | |
| 4,660,337 A | 4/1987 | Ross, III et al. | |
| 4,729,198 A | 3/1988 | Nethery | |
| 4,897,970 A | 2/1990 | Double et al. | |
| 5,170,599 A | 12/1992 | Knight | |
| 5,288,266 A | 2/1994 | Halley | |
| 5,354,569 A * | 10/1994 | Brown et al. | 426/411 |
| 5,363,605 A | 11/1994 | Handwerker | |
| 5,589,257 A * | 12/1996 | Carriker et al. | 442/381 |
| 5,669,732 A | 9/1997 | Truitt | |
| 5,887,409 A * | 3/1999 | Leal Pereira Da Silva | 53/434 |
| 6,164,453 A * | 12/2000 | Perkins | 206/596 |
| 6,198,106 B1 | 3/2001 | Barney et al. | |
| 6,494,324 B2 * | 12/2002 | Ours et al. | 206/527 |
| 6,575,629 B1 * | 6/2003 | Perkins | 383/105 |
| 6,609,354 B1 | 8/2003 | Villers | |
| 6,941,727 B2 | 9/2005 | Villers et al. | |
| 7,055,293 B2 * | 6/2006 | Ours et al. | 53/399 |
| 7,788,968 B2 | 9/2010 | Villers et al. | |
| 7,921,624 B2 * | 4/2011 | Ours et al. | 53/399 |
| 7,938,283 B2 | 5/2011 | Villers et al. | |
| 8,141,328 B2 * | 3/2012 | Villers et al. | 53/410 |
| 2003/0152671 A1 | 8/2003 | Johnstone | |
| 2005/0208157 A1 * | 9/2005 | Navarro et al. | 424/756 |
| 2006/0198861 A1 | 9/2006 | Villers et al. | |
| 2008/0202213 A1 | 8/2008 | Villers et al. | |
| 2008/0299272 A1 | 12/2008 | Navarro et al. | |
| 2010/0192998 A1 | 8/2010 | Villers et al. | |

FOREIGN PATENT DOCUMENTS

| | | |
|---|---|---|
| IL | 160950 | 12/2008 |
| WO | WO-99/09824 | 3/1999 |
| WO | WO-99/28578 | 6/1999 |
| WO | WO-99/45787 | 9/1999 |

OTHER PUBLICATIONS

In the U.S. Patent and Trademark Office, Final Office Action in re: U.S. Appl. No. 11/368,803, dated Jun. 10, 2010, 14 pages.

In the U.S. Patent and Trademark Office, Office Action in re: U.S. Appl. No. 11/368,803, dated Oct. 28, 2009, 9 pages.

In the U.S. Patent and Trademark Office, Restriction Requirement in re: U.S. Appl. No. 11/368,803, dated Aug. 18, 2009, 7 pages.

GrainPro, Inc., "GrainPro SuperGrainbags," Jul. 2004, Concord, MA located [online] Retrived from the internet, <URL: http://www.grainpro.com/grainpro-supergrainbag.php>.

Rankin, Silage Density and Dry Matter Loss in Silo Bags, [online]. Retrieved from the internet, URL: http://www.uwex.edu/CES/crops/silobagdensity.htm>.

Sophie Mirabella Speech delivered on Jun. 7, 2007 to the Australian Wheat Board. [online] <URL: http://www.silobag.com.au/home/>.

Villers et al., "Development and Applications of the Hermetic Storage Technology," *Proceedings of the 9th International Working Conference on Stored Product Protection*, Oct. 15-18, 2006, Campinas, São Paulo, Brazil, Brazilian Post-Harvest Association—ABRAPOS, Passo Fundo, RX, Brazil, 2006, pp. 719-729 (ISBN 8560234004).

* cited by examiner

US 8,528,305 B2

FLEXIBLE ULTRA-LOW PERMEABILITY TRANSPORT SYSTEM AND METHOD

CROSS-REFERENCES TO RELATED APPLICATIONS

The present application is a Divisional of U.S. patent application Ser. No. 11/368,803, filed Mar. 6, 2006, which claims priority from U.S. Provisional Patent Application No. 60/658,586, filed on Mar. 7, 2005, the entire subject matter and contents of which are incorporated by reference herein in their entirety.

FIELD OF THE INVENTION

The present invention is directed to a system and method of hermetic storage and easy transport of commodities. More specifically, the present invention is directed to providing an insect- and mold-resistant method for use in storage and transportation of bagged dry commodities using a hermetic, portable container. The purpose of the present invention is to combine easy transport with safe storage for dry commodities such as seeds, pulses, oil seeds, nuts, and grains normally transported either in unprotected man-portable grain or seed bags or by mechanized handling using "Big Bags." The present invention provides a storage system having low permeability per unit area for oxygen, carbon dioxide, and water vapor. It is designed to preserve the original post-drying moisture content of the commodity, to retain beneficial volatiles of the commodity, to prevent ingress of oxygen, and to eliminate insect infestation, as well as eliminate the growth of molds during storage and transport.

BACKGROUND OF THE INVENTION

Protected storage is required for many agricultural commodities, such as cereal grains (wheat, corn, or rice), pulses, oilseeds, dried fruits, nuts, cocoa, coffee, and spices, as well as seeds for the above, partially processed food such as flours, semolina, and others, and feed. Such commodities must be protected from the direct and indirect effects of oxygen and/or an increase in moisture, each of which permits growth of insects and/or microorganisms.

It is recognized that when commodities are harvested, there is a high likelihood that insects may be present along with the harvested commodity. If left untreated, the insect population may undergo rapid growth, resulting in damage or contamination of the commodity.

One approach to prevent losses from insect infestation is to use contact pesticides, or fumigants, and to prevent fungi development by the use of chemical preservatives on the commodity during storage immediately after harvest or prior to shipping. The use of these pesticides and chemicals is undesirable, as many pesticides can have an adverse effect on the health of the user, the consumer or the environment, including earth's upper atmosphere, and further may cause the development of insect resistance to the pesticide.

Other solutions to the infestation problem include refrigeration or the use of large flexible, hermetically sealed enclosures during storage, referred to as Cocoons™ (GrainPro, Inc. Concord, Mass., USA). In some cases, vacuum is added for more rapid disinfestation, such as is described in U.S. Pat. No. 6,609,354 to Villers and U.S. Pat. No. 6,941,727 to Villers, all of which are incorporated by reference herein in their entireties.

Specifically, a bulk commodity is hermetically sealed in a flexible container or enclosure, such as that formed from a 0.032 inch, low gas-permeability, UV resistant food grade PVC sheet material. A vacuum is established in the enclosure by using a conventional commercial vacuum pump and set point regulator. The flexible container or enclosure prevents excessive stresses when evacuated as would occur with a rigid container by conforming to the shape of the enclosed commodity. An opening, which can be opened or closed by means such as a solenoid-controlled inlet valve, is fed to an ordinary vacuum pump, with, if needed, an appropriate filter at the hermetically sealed container end to prevent clogging or damage to the pump. The vacuum pump is allowed to run for an extended period of time so that either or both Oxygen and interstitial moisture inside are substantially removed, typically down to a vacuum of 25-100 mm Hg at room temperature representing a level equivalent to, at atmospheric pressure, 0.7-2.75% oxygen. At this time the valve is closed, and the hermetically sealed container becomes a large "vacuum pack," with periodic pumping as required to compensate for residual infiltration of air, eliminating any of the respective causes of degradation named above due either to direct or indirect effects of Oxygen. Further, any residual moisture in the absence of Oxygen will not as easily cause moisture-produced damage. Damage to the commodity can be prevented, at least in part, by restricting the metabolic activity of all biological agents, including insects, microflora, and the commodity itself.

In a particular implementation, a vacuum in the range of 25-100 mm $H_g$ is established in the enclosure at 20° C. or higher. The appropriate minimum temperature is based on the particular infesting biological contaminant(s) and the desired kill time of the biological contaminant(s). The commodity can have a weight in the range of one-half to two hundred metric tons.

However, the Cocoons™ are restricted by the requirement that they be sufficiently hermetic to allow a low oxygen atmosphere to develop due to insect and/or commodity respiration and to prevent significant moisture ingress in humid atmospheres. The use of large bags provides more volume/surface area and as such, lowers permeability per ton. Thus, the smallest feasible Cocoons™ are limited by permeability considerations of available robust and moderately priced materials to a minimum capacity of about 7.5 cubic meters in bags with approximate dimensions of 2 m×3 m×1.5 m. Alternatively, flexible enclosures may be constructed somewhat smaller with a minimum volume of 0.7 $m^3$, such as the product GrainSafes™ (GrainPro, Inc. Concord, Mass., USA), as described more fully in Israeli Patent Number 122456, incorporated herein by reference in its entirety. However, this size involves compromises in the degree of permeability and therefore the ability to kill insects based on their, and the commodity's, respiration rates versus infiltration rates of oxygen from the outside. Thus, these enclosures are too large and too unstable to be readily transportable when full.

Bags which are easily human-portable are generally comprised of (high permeability) jute or woven polypropylene bags, and are typically in the 25 to 100 kg capacity. Machine transportable bags, known as "Big Bags," are generally in the 500 to 1000 kg capacity. Although flexible, such bags alone do not afford sufficient protection from infestation or molds, do not result in a low oxygen atmosphere, or prevent the effects of absorbing moisture from the atmosphere.

The material used for the Cocoons™ described above is a food grade flexible PVC plastic typically 0.83 mm thick, sold commercially by GrainPro under the trade name of Cocoon™ and for the smaller container, GrainSafe™. This PVC material is not suitable for long-term storage of small quantities; it is relatively too permeable, expensive and too stiff to be used in individual bags below five ton size without significantly compromising performance. Alternatively, semi-rigid aluminum bags, commonly known as "Joseph" bags, have long been available, and are comprised of relatively rigid aluminum coated plastic. These "Joseph" bags, however, are expensive, easily punctured, difficult to close, and do not protect against insect penetration, making them a less than optimal choice. Other forms of hermetic enclosure include amphores (large earthenware containers) as used in ancient times, lined underground pits sealed with a variety of substances, and metal or plastic drums. None are lightweight, flexible, inexpensive and easily transportable.

SUMMARY OF THE INVENTION

According to one aspect of the invention, there is provided a system for storage and transport of a commodity. The system includes a commodity for long-term storage having a weight of 10-2000 kg, a long-term storage container for containment and hermetic sealing of the commodity therein, the long-term storage container having at least one outer layer, at least one inner layer, and a middle layer comprised of an ultra-low permeability material, and an outer container for containment of the long-term storage container, wherein the outer container is configured to protect the long-term storage container during transport.

The long-term storage may include a storage period of at least four months or up to several years if the commodity is sufficiently dry. According to further features, the outer layer and inner layer are made of a flexible material, such as a polymeric material, for example, polyethylene. The middle layer may be comprised of nylon, EVOH, or any other suitable ultra-low permeability material or materials. According to further features, the commodity can have a weight of 10-100 kg, or of 250-2000 kg, for example. The outer container may be, for example, a jute bag, a polypropylene bag, or other commonly used bag for transport.

According to further features of the present invention, the long-term storage container may further include a compound of botanic origin, such as an essential oil, or a synthetic pesticide, to provide an insect repellent barrier to further prevent the possibility for insect infestation and/or penetration. The commodity can be seeds, cereals, oilseeds, coffee, cocoa, dry granular agricultural products, flours, or any other typically stored dry food or feed commodity.

According to another aspect of the present invention, there is provided a method for storage and transport of a commodity. The method includes placing the commodity in a long-term storage container having an outer layer, an inner layer, and a middle layer comprised of an ultra-low permeability material or materials, hermetically sealing the long-term storage container, and placing the long-term storage container in an outer container.

According to further features of the present invention, the method may further include transporting the commodity in the long-term storage container and the outer container using conventional bag handling methodologies. In one embodiment, the outer container is placed into an unaltered standard shipping container. The hermetic sealing can be done by twisting or rolling an open end of the long-term storage container and clamping the twisted end to maintain hermeticity, or by heat sealing an open end of the container.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

Figure 1A:
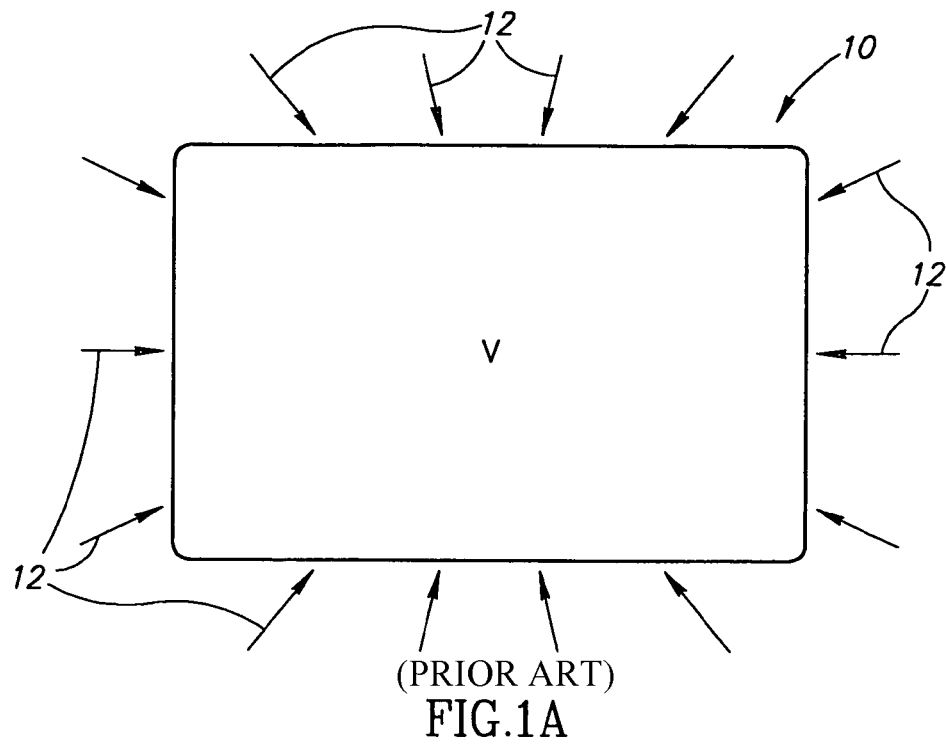
FIG. 1A is an illustration of a large storage container for storing of a commodity.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention relates to flexible reusable portable storage containers which have very low permeability to air, $CO_2$ and water vapor as described below, and which can be used for both short or long term storage and subsequent transportation of dry commodities. Such containers are referred to hereinbelow as "long-term storage containers" since they are capable of storing commodities for at least four months. However, it should be readily apparent that the "long-term storage containers" are not limited to long-term storage, and may be used for storage of commodities for any suitable period of time.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Figure 1B:
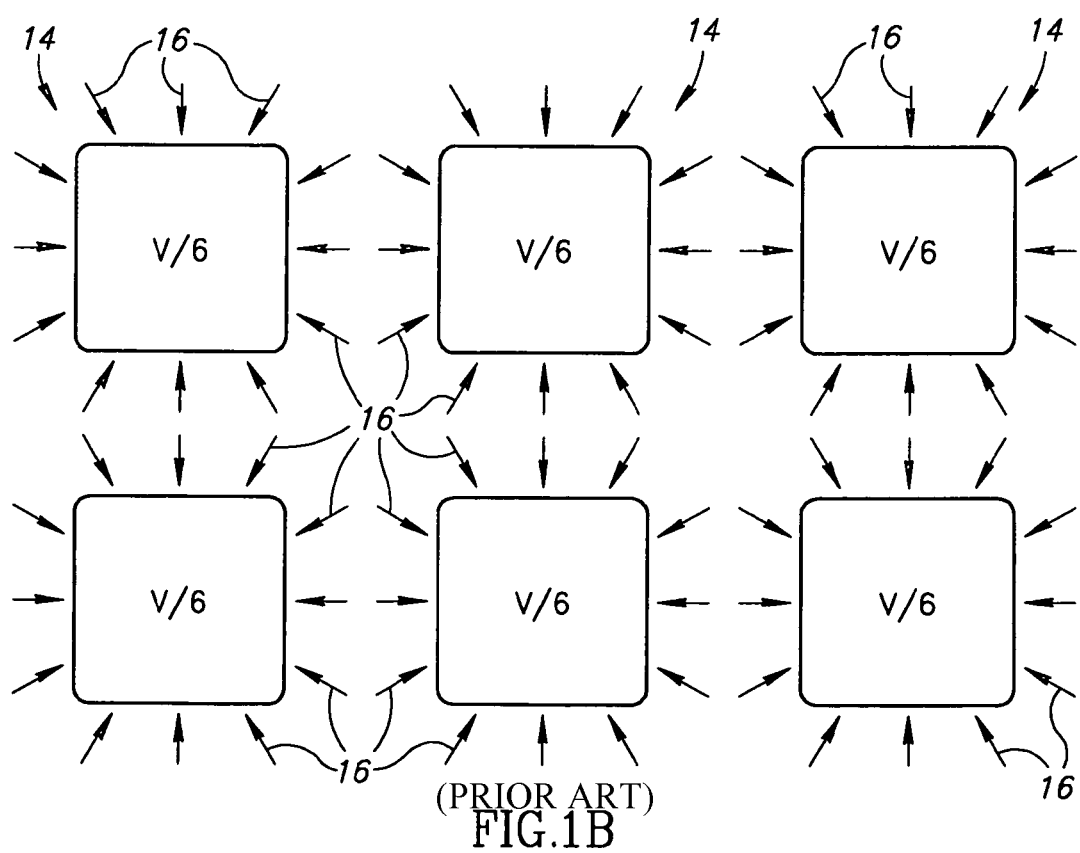
FIG. 1B is an illustration of multiple small storage containers, for alternative storing of the commodity of FIG. 1A.

Reference is now made to FIGS. 1A and 1B, which are illustrations of storage containers for a commodity, showing the relative permeability per volume for a single large bag versus multiple small bags. As shown in FIG. 1A, a large storage container 10, which can hold a particular volume V of commodity, will have a certain permeability per unit area, depicted by arrows 12. As shown in FIG. 1B, the same volume of commodity can be split up into several small bags 14, wherein a fraction of the overall volume is present in each of small bags 14. For the purpose of illustration, six small bags 14 are shown, each having a volume of V/6. The total permeability, as depicted by arrows 16, will be greater for the six small bags 14 than for the large storage container 10, since the overall surface area is greater. Thus, in order to enable use of smaller bags, overall permeability characteristics of the material must be decreased. For the purposes of the present invention, permeability refers to permeability to $O_2$, $CO_2$ and water vapor. However, it should be readily apparent that overall permeability to other substances would similarly vary with bag size.

In order to solve the problem of higher permeability associated with small storage containers, the present invention is directed to the use of an ultra-low permeability packaging material for purposes of long-term storage and transport of commodities. Although such materials are commonly used in the retail food industry, the low-permeability requirements of the materials used for retail packaging are much less demanding than long-term storage requirements. Thus, very small packages, on the order of less than 5 kg, are feasible for retail food packaging and are commonly used. However, the use of ultra-low permeability packaging materials for long-term storage and transport necessitates the use of storage containers which are significantly larger than retail food packages, but can be much smaller than the currently used long-term storage containers such as Cocoons™. These types of materials have not previously been used for long-term storage and transport.

Figure 2:
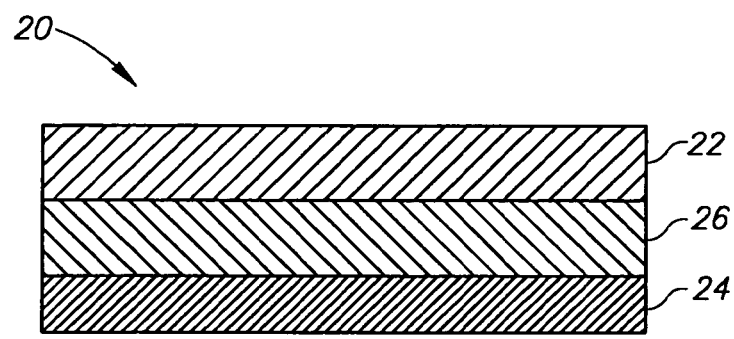
FIG. 2 is a cross-sectional illustration showing the layers of a material for use as a storage container.

Reference is now made to FIG. 2, which is a cross-sectional illustration of a material 20 for use in accordance with one embodiment of the present invention. Material 20 includes an outer layer 22 and an inner layer 24, with a middle layer 26 sandwiched between outer and inner layers 22 and 24. In accordance with embodiments of the present invention, outer layer 22 and inner layer 24 are co-extruded with middle layer 26. The purpose of middle layer 26 is to provide low permeability, while the outer and inner layers 22 and 24 are designed to add strength to middle layer 26.

In one embodiment, co-extruded plastic outer layer 22 and inner layer 24 are comprised of polymeric material, such as polyethylene, while middle layer 26 is comprised of a very low permeability material, such as, for example, nylon. An example of such a co-extruded material is Plastobarr N 80, manufactured and sold by Plastopil Ltd., Hazorea, Israel, originally designed for chemical and bacteriological warfare protection and now also used in retail vacuum packaging of meats, fish, or cheese ("vacuum pouches") to preserve freshness, and also used in retail packaging for preserving freshness of fresh vegetables. This material includes a thin co-extruded flexible triple-layer material (PE/PA/PE), including an outer layer and an inner layer of one polymeric material (polyethylene), and a very low permeability middle layer sandwiched between the two outer layers.

In some embodiments, any one or several of outer layer 22, inner layer 24 and middle layer 26 may include multiple layers of material. In one embodiment, inner layer 24 is nylon. In another embodiment, inner layer 24 is EVOH. In yet another embodiment, middle layer 24 is comprised of a combination of two or more materials. For example, a material which has low permeability to oxygen, but not to moisture may be combined with a material which has low permeability to water but not to oxygen. It should be readily apparent that middle layer 24 may be comprised of any low permeability barrier material suitable for sandwiching between an outer layer and an inner layer.

In one embodiment, material 20 may additionally include a coating or impregnation of a compound of botanic origin to improve resistance to insect penetration. An example of a natural pesticide suitable for impregnation or coating is an essential oil such as produced by Biopack, Ltd. (Caesaria, Israel) and described more fully in U.S. Patent Publication US2005-0208157, filed 5 Apr. 2004, Ser. No. 10/816,861 and Israel Patent Application Number 160950, both of which are incorporated herein by reference in their entireties. This insect repellent material is intended to further prevent possible insect penetration of the liner.

Methods for impregnating plastic films with essential oils are known in the art, and are described in, for example, U.S. Patent Publication Number US-2005-0208157-A1. Specifically, a composition of matter suitable for fabricating polymer-based packaging materials can be generated by mixing ar-trumerone sesquiterpene alcohols and/or turmeric oleoresin solid residue with polymers as a melt, by solvent compounding, or by immobilization or covalently linking of these compounds to the polymers. A composition of matter suitable for fabricating paper based packaging materials can be generated by adding ar-turmerone sesquiterpene alcohols and/or turmeric oleoresin solid residue to a paper pulp emulsion or impregnating paper, paperboard or textile substances with these compounds using methods well known in the art (e.g. spraying, dipping). A composition-of-matter suitable for fabricating flexible packaging materials, composed mainly of laminates, can be generated by adding ar-turmerone, sesquiterpene alcohols and/or turmeric oleoresin solid residue to any adhesive or ink or lacquer or any other additive between the laminate layers or to any coating on the laminate.

For non-food or feed products, such as seeds, a synthetic pesticide may be used, such as, for example, Deltamethrin (commercially available from Sumitomo Chemical Company, Tokyo, Japan), but with greater precautions and limitations because of potential toxicity.

Bags manufactured from this or similar material will have a very low permeability to Oxygen, Carbon Dioxide, and water vapor, even when the total thickness is under 0.1 mm. Thus, the permeability per unit area for Oxygen is reduced 8 to 10 fold or more over the permeability per unit area of the Cocoons™ typically from 400 $cc/m^2/day$ to 50 $cc/m^2/day$ or less for oxygen, while maintaining water vapor permeability of 9 $grams/m^2/day$ or less. The term "ultra low permeability" for purposes of the present invention thus refers to permeability to Oxygen of less than 100 $cc/m^2/day$ and to water vapor less of than 15 $g/m^2/day$. A container with ultra low permeability can have capacities ranging from 10 kg to 2,000 kg and preferably in a range of 20 kg to 1000 kg. The use of ultra low permeability containers enables the use of relatively small portable bags for hermetic storage and transport, which enhances portability, flexibility, and practicality as compared to hermetic storage and transport using Cocoons™.

Figure 3:
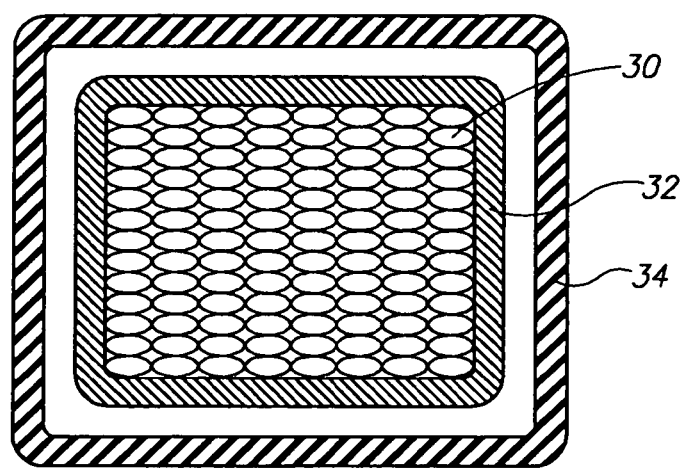
FIG. 3 is a cross sectional illustration of a long-term storage container placed inside a protective outer container.

To compensate for the relative mechanical fragility of containers or bags such as the ones of the present invention, these containers may be used as liners inside protective outer containers for transport and handling, as illustrated in FIG. 3 in cross section. As shown in FIG. 3, a commodity 30 is placed inside a long-term storage container 32, comprised of ultra-low permeability material 20. In one embodiment, long-term storage container 32 is capable of holding commodities within a range of 10-2000 kg. In one embodiment, long-term storage container 32 is capable of holding commodities within a range of 10-100 kg. In another embodiment, long-term storage container 32 is capable of holding commodities within a range of 250-2000 kg. Long-term storage container 32 is then placed in an outer container 34, which is used for transport.

Alternatively, material 20 is used to line outer container 34 prior to introduction of commodity 30 therein. Outer container 34 may be, for example, comprised of Jute (burlap) or woven polypropylene as conventionally used in the grain trade, typically containing around 50 kg of commodity, such as those commercially available from NYP Corp, Elizabeth, N.J., USA. Alternatively, outer container 34 may be a "Big Bag" designed for mechanized-handling typically up to 1000 kg capacity (commercially available from Palrig Plastic Industries, Kibbutz Naot Mordechai, Israel or B.A.G. Corp., Dallas, Tex., USA) or a similar bag designed for greater capacities. Any other suitable flexible transport bag, or a bin or box may be used as outer container 34. In an alternative embodiment, multiple long-term storage containers 32 may be placed into one outer container 34.

Figure 4:
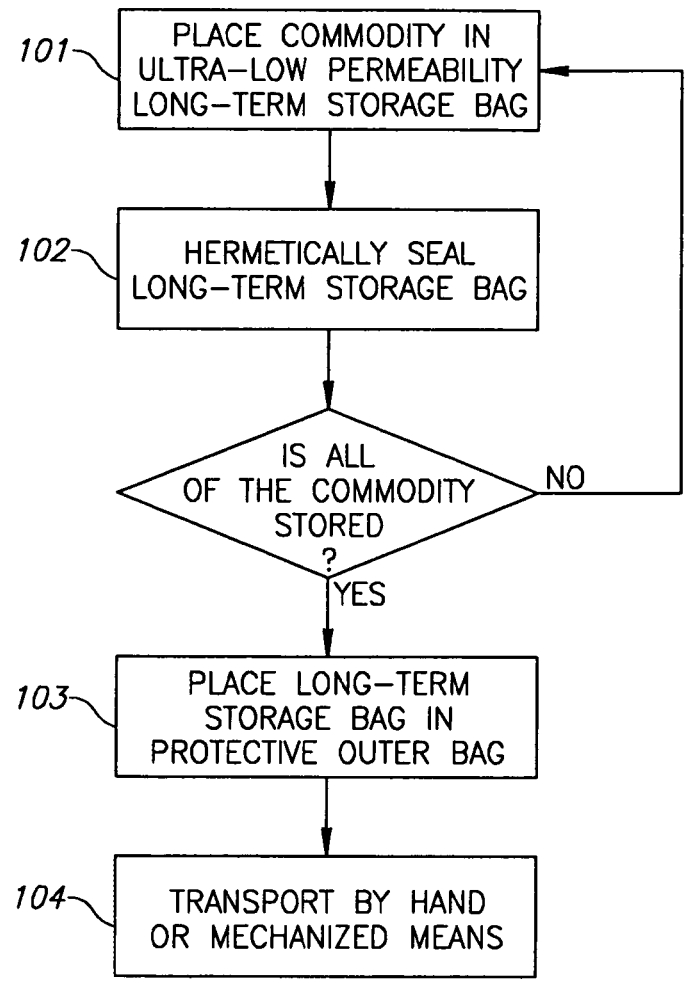
FIG. 4 is a flow chart illustration of the steps of a method for storage and transport of commodities, in accordance with one embodiment of the present invention.

Reference is now made to FIG. 4, which is a flowchart illustration of the steps of a method for storage and transport of commodities, in accordance with one embodiment of the present invention. First, the commodity is placed (step 101) into long-term storage container 32, in one embodiment comprised of a triple layer co-extruded film, as described above. In another embodiment, the long-term storage container 32 additionally includes impregnated or coated insecticide. Next, long-term storage container 32 is hermetically sealed (step 102). The sealing can be done by twisting an open end of the container and clamping the twisted end. Alternatively, sealing can be done by rolling an open end of the container and clamping the rolled end. Hermetic sealing can also be accomplished by heat sealing an open end of the container. The steps of placing and sealing are repeated until the entire commodity is in a storage container 32. Each of the long-term storage containers 32 is then placed (step 103) in one or more conventional protective outer containers 34 for protection in handling and transport. Infesting insects including eggs, larva, pupae, and adult insects at room temperature or above consume the available oxygen in a period of days to a few weeks and die in the same manner as in the previously referenced Cocoons™. The moisture level of the commodity remains substantially constant regardless of exterior humidity levels. Thus, commodities are hermetically enclosed in flexible portable containers which are insect-free and in which mold and fungus growth is inhibited due to maintaining sufficiently low moisture level and/or low Oxygen level as well as, in some cases, the protective effect of out-gassing of the commodity and the generation of $CO_2$ from the commodity and/or insects, while suitable for transport. Lastly, commodities which are inside storage containers 32 and further inside protective outer container 34 may be transported (step 104) by hand or by mechanized means. The transporting can be done by conventional bag handling methodologies, and may be done by placing the outer container into an unaltered standard shipping container.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. An insect and mold resistant method without the use of pesticide for long-term storage and transport of a dry agricultural commodity having a weight of 10-2,000 kilograms, the method comprising:

providing a flexible, hermetic long-term storage container for containment and hermetic sealing of the dry agricultural commodity therein, the flexible, hermetic long-term storage container comprising:
an outer layer;
an inner layer; and
a middle layer;
providing the middle layer comprising an ultra-low permeability packaging material;
providing the long-term storage container in a size to hold the commodity having a weight of 10-2,000 kilograms;
providing the ultra-low permeability packaging material with ultra-low permeability characteristics based upon 1) the size of the container, and 2) long-term storage requirements;
providing the ultra-low permeability material with ultra-low permeability characteristics including having a permeability to oxygen of less than 50 $cc/m^2/day$;
providing the ultra-low permeability packaging material with ultra-low permeability characteristics including having a permeability to water vapor of less than 15 $g/m^2/day$ such that said container is hermetic to water vapor;
providing the ultra-low permeability packaging material with a thickness of less than or equal to 0.1 mm;
providing the commodity with protection from insect infestation without use of a pesticide;
providing an outer container for containment of said long-term storage container, wherein the outer container mechanically protects the flexible, hermetic long-term storage container during handling and transport;
placing the dry agricultural commodity, having a weight of 10-2,000 kilograms, in the flexible, hermetic long-term storage container;
hermetically sealing the flexible, hermetic long-term storage container and limiting the oxygen ingress to less than the oxygen consumed by respiration;
resisting insect penetration of the storage container solely based upon the ultra-low permeability packaging material and without the use of a pesticide;
killing insects through lack of a continuous supply of oxygen by sufficiently preventing oxygen from entering the container as solely a result of the ultra-low permeability characteristics;

preventing mold growth as a result of the ultra-low permeability characteristics;

maintaining the original post-drying moisture content of the dry agricultural commodity for commodities having the weight of 10-2,000 kilograms and for long-term storage of at least four months solely based upon the ultra-low permeability packaging material, without the use of pesticide, and without the use of periodic vacuum pumping after hermetically sealing the container;

protecting against insect infestation solely through the use of the ultra-low permeability material, wherein the available oxygen is consumed by infesting insects including eggs, larva, pupae, and adult insects to a level low enough to cause the death of the infesting insects;

protecting the commodity in the hermetically sealed storage container by inhibiting mold and fungus growth through the low level of oxygen and lack of a high humidity; and placing the flexible, hermetic long-term storage container in the outer container.

2. The method of claim 1, wherein the flexible, hermetic long-term storage container has a 10 to 100 kilogram capacity.

3. The method of claim 1, in which the hermetically sealing is done by one of:

twisting an open end of the flexible, hermetic long-term storage container and clamping the twisted end to maintain hermeticity;

rolling an open end of the flexible, hermetic long-term storage container and clamping said rolled end to maintain hermeticity; and heat sealing an open end of the flexible, hermetic long-term storage container.

4. The method of claim 1, further comprising:

transporting said dry agricultural commodity in said flexible, hermetic long-term storage container and said outer container using conventional bag handling methodologies.

5. The method of claim 1, wherein the outer and inner layers are comprised of polymeric material.

6. The method of claim 5, wherein the polymeric material of the outer layer is polyethylene.

7. The method of claim 1, wherein the inner layer comprises nylon.

8. The method of claim 1, wherein the inner layer comprises EVOH.

9. An insect and mold resistant method without the use of pesticide for long-term storage and transport of a dry agricultural commodity having a weight of 10-2,000 kilogram, the method consisting of the steps of:

providing a flexible, hermetic long-term storage container for containment and hermetic sealing of the dry agricultural commodity therein, the flexible, hermetic long-term storage container comprising:
an outer layer;
an inner layer; and
a middle layer;

providing the middle layer comprising an ultra-low permeability packaging material;

providing the long-term storage container in a size to hold the commodity having a weight of 10-2,000 kilograms;

providing the long-term storage container in a size to hold the commodity having a weight of 10-2,000 kilograms;

providing the ultra-low permeability packaging material with ultra-low permeability characteristics based upon 1) the size of the container, and 2) long-term storage requirements;

providing the ultra-low permeability material with ultra-low permeability characteristics including having a permeability to oxygen of less than 50 $cc/m^2/day$;

providing the ultra-low permeability packaging material with ultra-low permeability characteristics including having a permeability to water vapor of less than 15 $g/m^2/day$ such that said container is hermetic to water vapor;

providing the ultra-low permeability packaging material with a thickness of less than or equal to 0.1 mm;

providing the commodity with protection from insect infestation without use of a pesticide;

providing an outer container for containment of said long-term storage container, wherein the outer container mechanically protects the flexible, hermetic long-term storage container during handling and transport;

placing the dry agricultural commodity, having a weight of 10-2,000 kilograms, in the flexible, hermetic long-term storage container;

hermetically sealing the flexible, hermetic long-term storage container and limiting the oxygen to available oxygen inside the container;

resisting insect penetration of the storage container solely based upon the ultra-low permeability packaging material and without the use of a pesticide;

killing insects through lack of a continuous supply of oxygen by sufficiently preventing oxygen from entering the container solely based upon the ultra-low permeability packaging material;

preventing mold growth as a result of the ultra-low permeability characteristics;

maintaining the original post-drying moisture content of the dry agricultural commodity for commodities having the weight of 10-2,000 kilograms and for long-term storage of at least four months solely based upon the ultra-low permeability packaging material, without the use of pesticide, and without the use of periodic vacuum pumping after hermetically sealing the container;

protecting against insect infestation solely through the use of the ultra-low permeability material, wherein the available oxygen is consumed by infesting insects including eggs, larva, pupae, and adult insects to a level low enough to cause the death of the infesting insects;

protecting the commodity in the hermetically sealed storage container by inhibiting mold and fungus growth through the low level of oxygen and lack of a high humidity; and placing the flexible, hermetic long-term storage container in the outer container.

* * * * *